United States Patent [19]
Lin et al.

[11] Patent Number: 6,071,745
[45] Date of Patent: Jun. 6, 2000

[54] METHOD AND FORMULATION FOR LYOPHILIZING CULTURED HUMAN CELLS TO PRESERVE RNA AND DNA CONTAINED IN CELLS FOR USE IN MOLECULAR BIOLOGY EXPERIMENTS

[75] Inventors: Ching-I Patsy Lin, Hercules; Robert Bruce Wallace, Greenbrae, both of Calif.; Jeffrey Cossman, Potomac, Md.; Cynthia French, Irvine, Calif.

[73] Assignee: Bio-Rad Laboratories, Hercules, Calif.

[21] Appl. No.: 08/884,029

[22] Filed: Jun. 27, 1997

[51] Int. Cl.[7] .............................. C12N 5/02; C12N 5/00; C12N 5/08
[52] U.S. Cl. ................... 435/374; 435/372.3; 435/372
[58] Field of Search ............................ 435/374, 372.3, 435/372

[56] References Cited

U.S. PATENT DOCUMENTS

| | | | |
|---|---|---|---|
| 4,520,113 | 5/1985 | Gallo et al. | 436/504 |
| 5,059,518 | 10/1991 | Kortright . | |
| 5,409,826 | 4/1995 | Maples et al. | 435/240.2 |
| 5,525,715 | 6/1996 | Racaniello et al. | 536/23.72 |

FOREIGN PATENT DOCUMENTS

| | | |
|---|---|---|
| 0 508 496 A1 | 10/1992 | European Pat. Off. . |
| 0 356 257 B1 | 3/1995 | European Pat. Off. . |
| 0 469 766 B1 | 12/1995 | European Pat. Off. . |

OTHER PUBLICATIONS

Chemical Abstracts 122 (13) :158688c.

Chomczynski, Piotr (1993) "A Reagent for the Single–Step Simultaneous Isolation of RNA, DNA and Proteins from Cell Tissue Samples", *BioTechniques* 15(3) :532–535.

Gill, Santokh S., et al. (1996) "Ensuring Revovery of Intact RNA from Rat Pancreas", *Molecular Biotechnology*, 6:359–362.

Jennings, Thomas, A. (1997) "Effect of formulation on lyophilizatoin, part 1", *IVD Technology* 3(1) :38–42.

Jennings, Thomas, A. (1997) "Effect of formulation on lyophilization, part 2", *IVD Technology* 3(2) :42–49.

Greaves, R.I.N. (1964) "Fundamental aspects of freeze–drying bacteria and living cells", *Aspects Théoriques et Industriels de la lyophilisation*, 407–410.

*Primary Examiner*—Francisco Prats
*Attorney, Agent, or Firm*—Townsend and Townsend and Crew LLP

[57] ABSTRACT

The present invention relates to methods for lyophilizing eukaryotic cells and isolating intact nucleic acids from such cells, and related kits for using the same.

11 Claims, 2 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

GACATGGAAG CCATCACAGA C                                         21

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:2:

CGACCGTTCA GCTGGATATT AC                                      22

(2) INFORMATION FOR SEQ ID NO:3:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:3:

GAAGTGTTTC AGAAGCTTCT CC                                      22

(2) INFORMATION FOR SEQ ID NO:4:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

TGGAGCTGCA GATGCT                                                       16

(2) INFORMATION FOR SEQ ID NO:5:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

TGATTATAGC CTAAGACCCG GA                                                        22

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:6:

ATCTCCACTG GCCACAA                                                              17

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

CCTCCATGAT GCTGCTTACA TGTC                                                      24

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

ATGTCTCGCT CCGTGGCCTT AGCT                                                      24

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 13..18
            (D) OTHER INFORMATION: /mod_base= OTHER
                /note= "t at positions 13-18 may be
                present or absent"

(xi) SEQUENCE DESCRIPTION: SEQ ID NO:9:

TTTTTTTTTT TTTTTTTT                                                             18

METHOD AND FORMULATION FOR LYOPHILIZING CULTURED HUMAN CELLS TO PRESERVE RNA AND DNA CONTAINED IN CELLS FOR USE IN MOLECULAR BIOLOGY EXPERIMENTS

CROSS-REFERENCE TO RELATED APPLICATIONS

Not applicable.

FEDERALLY SPONSORED RESEARCH OR DEVELOPMENT

Not applicable.

FIELD OF THE INVENTION

The present invention relates to methods for lyophilizing eukaryotic cells and isolating intact nucleic acids from such cells, and kits for using the same.

BACKGROUND

Methods of lyophilizing or "freeze-drying" viruses, biologically active molecules, and bacteria are routinely used in laboratories. Typically, the cells or molecules to be lyophilized are suspended in a solution that allows recovery of the desired activity after the freezing process. Ideal formulations for lyophilization solutions should provide a stabilizing environment for a finite time before lyophilization; provide good thermal and freezing properties during lyophilization; and cryoprotect the desired activity.

Previous methods of lyophilization have focused primarily on using sugars in preservation of proteins in eukaryotic cells and preservation of bacteria. For example, the primary ingredient of solutions for lyophilizing bacterial cells is a sugar at a concentration of 5–10%, used to stabilize the cells (Greaves, *Fundamental Aspects of Freeze-drying Bacterial and Living Cells*, in *Aspects Theoriques et Industriels de la Lyophilisation*, 407–410 (Rey ed. 1964). However, effective eukaryotic cell lyophilization methods for preserving nucleic acids, particularly RNA, have not been established. The inclusion of sugar such as lactose in an isotonic eukaryotic cell lyophilization formulation did not give high yields of nucleic acid isolated from lyophilized cells. The inclusion of preserving materials, such as low concentrations of methanol or ethanol in the lyophilization solutions was also found to be ineffective for isolation of intact nucleic acid after lyophilization.

Methods of long term preservation of nucleic acids from eukaryotic cells are desirable due to the use of molecular biological approaches for disease diagnosis and forensics. In such assays, positive and negative controls from a reference source are particularly useful. Clinical samples from previous patients and cell lines with known genotypes are often used as sources of experimental control cells. However, clinical samples from patients are typically available in limited amounts. Cultured cell lines are convenient sources of control cells, however, the use of freshly cultured cells for each assay is problematic because of the time, cost, and labor needed for growth and maintenance of cultured cells.

SUMMARY OF THE INVENTION

The present invention therefore provides an isotonic solution that is nuclease free and is used as a lyophilization solution for eukaryotic cells, allowing isolation of intact DNA and RNA from the cells. This invention is useful for long term storage and preservation of nucleic acid from eukaryotic cells. The invention also provides standard nucleic acid samples for use as controls in assays such as diagnostic and forensic assays.

In one aspect the invention provides a method for long term preservation of nucleic acid contained within eukaryotic cells, the method comprising the steps of: (1) lyophilizing an aqueous solution of intact eukaryotic cells where said solution is isotonic to the cells and is nuclease free; and (2) maintaining the lyophilized cells under sealed conditions sufficient to avoid contact with atmospheric humidity.

In one embodiment, the aqueous solution has been treated with diethyl pyrocarbonate. In another embodiment, the aqueous solution comprises sodium chloride at a concentration of between 0.8 and 1.% by weight to volume. In yet another embodiment, the aqueous solution comprises a standard phosphate buffered saline solution. In a further embodiment, the pH of the solution is between 6.8 and 8.2.

In one embodiment, the eukaryotic cells are mammalian. In another embodiment, the cells are human. In yet another embodiment the cells are lymphocytes. In a further embodiment, the cells are infected with an RNA virus. In a further embodiment, the cells are cultured prior to lyophilization.

In another aspect, the invention provides a method for isolating intact nucleic acid from lyophilized cell comprising the steps of: (1) lyophilizing an aqueous solution of living eukaryotic cells where said solution is isotonic to the cells and is nuclease free; (2) maintaining the lyophilized cells under sealed conditions for at least 30 days; (3) unsealing the cells; (4) denaturing the cellular proteins to create a mixture of intact nucleic acid and denatured cellular proteins; and (5) isolating intact nucleic acid from the mixture of denatured cellular proteins and nucleic acid with the proviso that the cells are not revived.

In one embodiment, the isolated nucleic acid is ribonucleic acid. In another embodiment, the cells are lymphocytes.

In another aspect the invention provides a collection of standardized, sealed vials containing lyophilized eukaryotic cells for use as controls in diagnostic assays wherein the cells after 4 weeks at $-20°$ C. have more than 50% of their 18S rRNA intact as measured by gel electrophoresis.

In one embodiment, the cells are lymphocytes. In another embodiment, the cells are infected with an RNA virus. In a further embodiment, the vial contains an inhibitor of RNase in an amount effective to reduce degradation of RNA.

In another aspect the invention provides a nucleic acid hybridization kit comprising lyophilized eukaryotic cells.

In one embodiment, the cells are human. In another embodiment, the cells are lymphocytes. In yet another embodiment, the cells are infected with an RNA virus.

In another embodiment, the kit further comprises cell free nucleic acid selected to hybridize to a known target nucleic acid. In yet another embodiment, the kit further comprises a labelled nucleic acid. In a further embodiment, the nucleic acid hybridization assay uses RNA extracted from the lyophilized cells.

In another embodiment, the nucleic acid hybridization assay is an amplification based assay. In yet another embodiment, the amplification based assay is a ligase chain reaction based assay or a polymerase chain reaction based assay. In a further embodiment, the kit further comprises at least one PCR primer pair. In another embodiment the kit further comprises reverse transcriptase. In yet another embodiment the RNA is transcribed into complementary DNA during the assay.

In another embodiment, the kit further comprises a vial containing the cells wherein the vial is sealed to prevent atmospheric humidity from contacting the cells.

DETAILED DESCRIPTION OF THE INVENTION

I. Introduction

Figure 1:
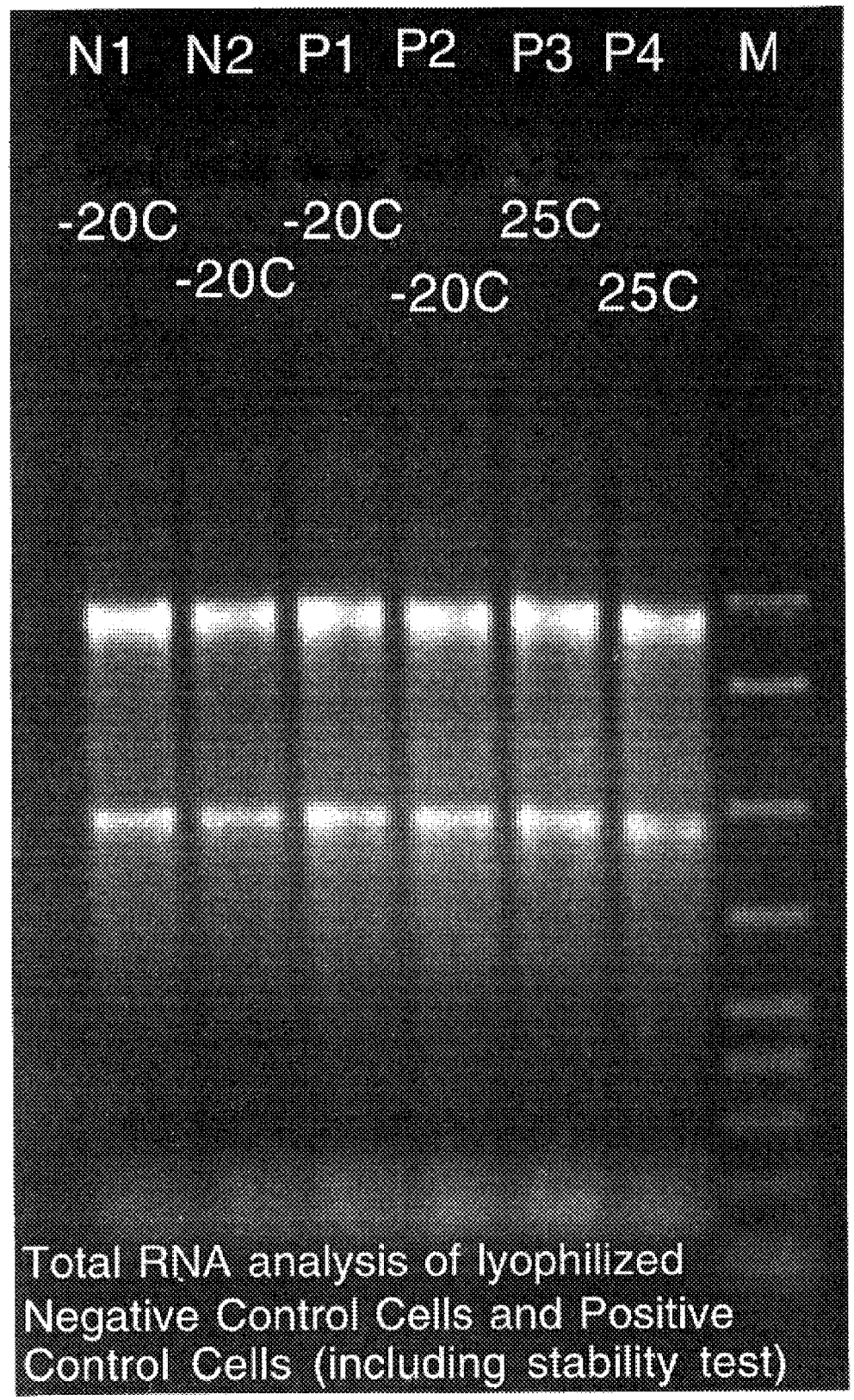
FIG. 1 shows a picture of an ethidium bromide stained gel with RNA isolated from cell samples that were lyophilized in DEPC treated 1× PBS. Lanes N1 and N2 contain RNA from HeLa S3 samples stored at −20° C. for 3 months; lanes P1 and P2 contain RNA from SAM-1 samples stored at −20° C. for 6 months; and lanes P3 and P4 contain RNA from SAM-1 samples stored at 25° C. for 2 days, which is equivalent to storage for 2 years at −20° C. (see stressed stability calculation below). This gel was scanned using a densitometer to determine the ratio of the 28S rRNA band to the 18S rRNA band.

This invention provides for a nucleic acid stable preparation of lyophilized cell for diagnostic kits. When cells are lyophilized in an isotonic solution, the nucleic acid is expected to be protected from all nucleases because the cell membrane reportedly maintains its integrity in the isotonic solution. We discovered that the nucleic acid rapidly degrades in cells lyophilized using the isotonic solutions of the prior art. Contrary to expectations, endogenous cellular nucleases are not significantly degrading the cellular nucleic acid. We surprisingly discovered that despite the use of an isotonic solution, the cells were rendered permeable to exogenous nucleases just prior to or during the short, cold lyophilization procedure. This problem of exogenous nucleases in the lyophilization buffer was solved by using lyophilization solutions that are nuclease free.

Pathologists often use molecular biological approaches to aid in the diagnosis of diseases such as cancer, genetic diseases, and infectious diseases. In addition, investigators in the field of forensics also use DNA probe and molecular analysis for criminal investigations and paternity determinations. This molecular analysis often takes the form of DNA or RNA isolation from eukaryotic cells, typically followed by amplification and gel electrophoresis. A major problem for these experiments is the lack of a standard cellular source for positive and negative nucleic acid controls. This invention provides lyophilized eukaryotic cells for use as controls in diagnostic and forensic analysis. These cells are lyophilized in an isotonic solution that is nuclease free because it has been treated with a nuclease inhibitor, or because it contains a nuclease inhibitor. This method of lyophilization provides a means of long term storage of the cells and allows isolation of intact nucleic acid from the cells, e.g., for use as controls in molecular biological assays.

II. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

"Long term preservation" refers to storage of lyophilized cells in such a manner that the nucleic acid is relatively undegraded and intact over a period of about a month or longer when stored at 25° C. or lower.

"Lyophilizing" refers to a process of freezing and drying a solution.

"Isotonic" refers to a solution that has the same water potential (the sum of the osmotic and the pressure potential) as the reference, e.g., a living cell, so that there is generally no net increase or decrease in the water content of the reference cell when it is in the solution and the cell membrane of the reference cell retains its integrity.

"Sealed conditions" refer to means of closing a container so that contact with atmospheric humidity is avoided.

"Standard phosphate buffered saline" refers to any scientifically acceptable formulation of saline buffered with phosphate, including commercially available formulations and formulations made from laboratory recipes.

"Cultured" refers to cells grown ex vivo.

"Intact nucleic acid" refers to nucleic acid that is substantially undegraded.

"Nuclease free" refers to a solution that is substantially free of nuclease so that intact nucleic acid can be recovered from cells after the cells have been resuspended in the solution and lyophilized. A nuclease free solution can be obtained either by using commercially available nuclease free reagents or by treating the solution used for lyophilization with a compound or process that is a specific or nonspecific nuclease inhibitor. Nonspecific nuclease inhibitors include, e.g., treatment of a solution with diethyl pyrocarbonate, which inactivates enzymes; or adding a chaotrophic reagent that denatures proteins such as guanidine isothiocyanate or sodium dodecyl sulfate ("SDS"). Specific nuclease inhibitors include RNase inhibitors such as placental RNase inhibitor enzyme (Blackburn, *J. Biol. Chem.* 254: 12484 (1970)); and vanadyl-ribonucleoside complexes.

A solution is defined as nuclease free by comparing RNA isolated from fresh (non-lyophilized) control cells and RNA isolated from lyophilized cells. RNA from the control and lyophilized cells is isolated according to the same procedures. The control cells are directly resuspended in RNA isolation buffer and are not contacted by the lyophilization solution. A solution is considered nuclease free if the integrity of 28S and 18S rRNA and the yield of total RNA from the lyophilized cells is within 90% of the integrity and yield of RNA from the control cells. For cultured cells and tissue samples such as blood, control cells are typically pelleted from culture medium using low speed centrifugation, and then directly resuspended in the RNA isolation buffer. For tissue samples, freshly isolated tissue is directly resuspended in the RNA isolation buffer.

"Nucleic acid" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. The polymers may be in either single- or double-stranded form. Thus, the term includes nucleotide polymers in which the nucleotides and the linkages between them include non-naturally occurring synthetic analogs. Such polynucleotides can be synthesized, for example, using an automated DNA synthesizer. The term nucleic acid is used interchangeably with gene, cDNA, and mRNA encoded by a gene. It will be understood that when a nucleotide sequence is represented by a DNA sequence (i.e., A, T, G, C), this also includes an RNA sequence (i.e., A, U, G, C) in which "U" replaces "T"

A nucleic acid selected to "hybridize" to a target nucleic acid hybridizes, duplexes or binds only to the particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.) (1989); Ausubel et al., *Current Protocols in Molecular Biology*, (1987)).

"Amplification" primers are oligonucleotides comprising either natural or analog nucleotides that can serve as the basis for the amplification of a target nucleic acid sequence. They include both polymerase chain reaction primers and ligase chain reaction oligonucleotides. Examples of amplification based assays or reactions include, e.g., reverse transcription, polymerase chain reaction, and ligase chain reaction.

"Labelled" refer to incorporation of a detectable marker, e.g., a radiolabelled nucleotide or a ligand such as biotinyl moieties that bind to avidin or streptavidin). Examples of labels include, but are not limited to, the following: radio-isotopes (e.g., $^3$H, $^{14}$C, $^{35}$S, $^{125}$I, $^{131}$I, $^{32}$P), fluorescent or phosphorescent labels (e.g., FITC, rhodamine), enzymatic labels (e.g., horseradish peroxidase, β-galactosidase, luciferase, alkaline phosphatase), biotinyl groups, and epitopes. In some embodiments, labels are attached by spacer arms of various lengths, e.g., to reduce potential steric hindrance.

III. Eukaryotic cells and cell culture

The methods of the invention are used to provide eukaryotic cells from which nucleic acid is isolated, typically for use as positive and negative controls in diagnostic and forensic assays. Any suitable eukaryotic cell can be lyophilized using this method, including cells derived from tissue in vivo and cells that have been cultured in vitro. Preferably, the cells are human cells.

Primary cells from tissue in vivo include e.g., tumor cells, hematopoietic cells, muscle cells, liver cells, and skin cells. Preferred primary cell types include cancer cells, hematopoietic cells (e.g., lymphocytes), and virally infected cells. Primary cells from tissue in vivo are isolated according to standard procedures, e.g., biopsy, dissection, aspiration, venipuncture, and scraping.

Cultured cells can be derived from primary explants, e.g., mouse embryos, chick embryos, neurons, astrocytes, hematopoietic cells, skin cells such as keratinocytes and fibroblasts, liver cells, muscle cells, tumor cells. Cultured cells can also come from established cell lines such as HeLa cells, SAM-1 cells, Dr11 cells, BALB/c cells, CHO cells, mouse L cell fibroblasts, COS cells, and BHK-21 cells. Cultured cells can also be infected with DNA or RNA viruses. Preferred cultured cell types include lymphocyte cell lines, virally infected cells, and tumor-derived cell lines. Explant cultures of primary cells are obtained and cultured according to standard procedures, as are cultured cell lines (see, e.g., Freshney, *Culture of Animal Cells* (3rd ed. 1994); Ausubel et al., supra, Appendix 3F).

The cell culture environment includes consideration of such factors as the substrate for cell growth, the gas phase, the medium, and temperature. Substrates for cell growth vary according to the manner in which the cell grows, e.g., attached to a substrate (monolayer cultures), in semi-solid media such as agarose, or in liquid (suspension cultures). For cells that grow attached to a substrate, typically plastic dishes or flasks are used. Other artificial substrates can be used such as glass and metals. The substrate is often treated by etching, or by coating with substances such as collagen, chondronectin, fibronectin, and laminin. Cell feeder layers and microcapillaries are also used. For nonadhesive cells that do not require attachment to a substrate, the cells can be plated in agar or grown in circulating media ("spinner" cultures). The type of culture vessel depends on the culture conditions, e.g., multi-well plates, petri dishes, tissue culture tubes, flasks, roller bottles, microcarriers, and spinner bottles. Cells are grown at densities that are determined empirically based on the cell type. For example, a typical cell density for a cell line such as HeLa varies from $1-10 \times 10^5$ cells per ml of medium.

The important constituents of the gas phase are oxygen and carbon dioxide. Typically atmospheric oxygen tensions are used for most cell cultures, although some cultures require higher or lower oxygen tensions. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1–10% in the incubator.

Cultured cells are normally grown in an incubator that provides a suitable temperature, e.g., the body temperature of the animal from which is the cells were obtained, accounting for regional variations in temperature (e.g., skin cells may prefer a slightly lower temperature). Generally, 37° C. is the preferred temperature for cell culture. Most incubators are humidified to approximately atmospheric conditions.

Defined cell media are available as packaged, premixed powders or presterilized solutions. Examples of commonly used media include RPMI 1640, DMEM, and McCoy's Medium (see, e.g., GibcoBRL/Life Technologies Catalogue and Reference Guide). Defined cell culture media are often supplemented with 5–20% serum, e.g., horse, calf, and fetal bovine serum. The culture medium is usually buffered to maintain the cells at a pH from 6.8–8.2, preferably pH 7.4. Other supplements to the media include, e.g., antibiotics, amino acids, sugars, and growth factors.

IV. Lyophilization procedures

After cells are isolated or grown in culture, they are prepared for lyophilization. Adhesive cells are removed from the culture substrate using standard techniques such as trypsin treatment. Cells that have been removed from a substrate or that are in a suspension culture are pelleted using low speed centrifugation and then resuspended in lyophilization solution according to standard procedures. Cells are resuspended in lyophilization solution at a concentration of about from $1 \times 10^4$ per ml to $1 \times 10^9$ per ml, preferably at a concentration of approximately $1 \times 10^6 - 10^7$ cells per ml.

The cells are resuspended in an isotonic lyophilization solution that is nuclease free. Nuclease and RNase inhibitors include e.g., treatment of a solution with diethyl pyrocarbonate ("DEPC"), placental RNase inhibitor enzyme (Blackburn, *J. Biol. Chem.* 254: 12484 (1970)), a chaotropic reagent that denatures proteins, vanadyl-ribonucleoside complexes, or clays such as macaloid. A preferred nuclease inhibitor is treatment of the lyophilization solution with DEPC. Typically, DEPC treated lyophilization solution is made by adding 0.05%–0.1% v/v DEPC to the solution in a container and then shaking the sealed container at room temperature for four hours to overnight. The solution is then autoclaved according to standard conditions and cooled. DEPC treated water can be used to make solutions that contain TRIS, since DEPC reacts with TRIS. Placental RNase inhibitor enzyme is used according to concentrations suggested by the manufacturer, e.g. 250–500 units/ml of solution. Vanadyl-ribonucleoside complexes are added according to concentrations suggested by the manufacturer.

The lyophilization solution is an isotonic solution that is generally compatible with methods and reagents used for nucleic acid isolation. Isotonic resuspension solutions such as phosphate buffered saline ("PBS") and TRIS buffered saline ("TBS") are examples of lyophilization solutions. The isotonic solution typically has a pH range of 6.8 to 8.3, preferably in the range of pH 7.2 to 7.4. The isotonic solution typically has a NaCl concentration in the range of about 0.1–0.2 M, or in the range of about 0.8 to 1.0% by weight per volume (w/v). Preferably the NaCl is at an concentration of 0.15 M or 0.9% w/v.

A preferred lyophilization solution is 1× PBS. Any standard formulation of 1× PBS can be used, either commercially available solutions or solutions made from a standard laboratory recipe. 1× PBS typically includes NaCl and phosphate ions at a pH of 6.8 to 8.3, preferably a pH of 7.2–7.4. The NaCl concentration is typically in a range of 0.1–0.2 M, or 0.8 to 1.0% w/v. 1× PBS can contain monobasic potassium phosphate, mono or dibasic sodium phosphate, and other phosphate salts in a range of about 10–40 mM phosphate, as well as sodium chloride, calcium chloride, and magnesium chloride. 1× PBS can also contain additional components such as sodium pyruvate (see, e.g., GibcoBRL/Life Technologies Product and Reference Guide; Ausubel et at., supra; Sambrook et al., supra). One formulation of 1× PBS contains 0.15 M NaCl (0.9% w/v) and 4 mM phosphate ion at a pH of 7.2 to 7.4. Another contains 137 mM NaCl, 2.7 mM KCl, 4.3 mM $Na_2HPO_4$, 1.4 mM $KH_2PO_4$, at pH 7.3 (Ausubel et al., supra).

Another suitable isotonic lyophilization solution is TBS. One formulation of TBS contains: 137 mM NaCl, 5 mM KCl, 0.5 mM $MgCl_2$, 25 mM TRIS base, 0.7 mM $Na_2HPO_4$, and 0.9 mM $CaCl_2$. Such solutions are commercially available and are sold in powder form or as premixed sterile solutions.

Once the cells are resuspended in the appropriate lyophilization solution, the cells are aliquoted in amounts from approximately 100 μl to 1 ml in suitable vials. Preferably, 100–500 μl of cells in solution are aliquoted per lyophilization vial. Larger or smaller aliquots of cells can be used according to the size of the lyophilization container and experimental need. The lyophilization vials are nuclease-free and sterile. Typically, sterile autoclaved glass or plastic vials are used, preferably glass vials. The vials are provided with caps or lids that can be sealed so that the cell sample avoids contact with atmospheric humidity. An example of a suitable cap is a plastic lid that is crimped around the edges with a metal ring after lyophilization is complete.

Cells are typically lyophilized using commercial, automated lyophilizers, although smaller non-automated lyophilizers can also be used. After the cells are resuspended in the lyophilization solution they are quick frozen before lyophilization at temperatures of −20° C. or below, preferable −40° C. Lyophilization conditions are determined empirically according to standard procedures depending on the machine, the lyophilization solution volume, and type of vial (see, e.g., Jennings, *IVD Technology* 3: 38–49 (1997). Typically the samples are lyophilized until dry, about 4 hours to 48 hours, typically 12–24 hours. The lyophilization typically takes place under a vacuum with pressures in the range of about 100 microns (millitorr) to 200 microns. The temperature of the lyophilization procedure typically starts about −20° C. to −40° C. and then typically gradually rises to about room temperature during the lyophilization process.

After the cells are lyophilized they are stored at a temperature from about 25° C. to about −70° C. Preferably, lyophilized cells are stored at about −20° C. or below. Storage temperatures can be determined according to standard procedures using real time and stressed stability tests. Stressed stability or accelerated stability is a test performed for preliminary determination of shelf life, typically confirmed with a follow-up real time stability study. The test is performed by stressing a sample at an elevated temperature and monitoring stability of the reagent. Calculations are then performed to relate the stability at the elevated temperature to that expected at an approved storage temperature using an appropriate model, such as the commonly used Arrhenius model.

The Arrhenius expression for decomposition kinetics specifies the rate constant of a reaction that obeys the relation $K_2=Ce^{-Ea/RT}$, where C is collision factor, R=1.9872, Ea is the activation energy (standard estimate 20 Kcal/mol), T is the temperature, and K is the time of decay. For a pseudo first order rate, the rate is $d[a]/dt=K[A]$ or $e^{(Ea/RT2-EaRT1)}=t2/t1$. According to this calculation, storage at 25° C. for 1 day is about equal to storage at −20° C. for 1 year. (see, e.g., Connors et al., *Chemical Stability of Pharmaceuticals, A Handbook for Pharmacists* (1979)).

V. Nucleic acid isolation

After the eukaryotic cells of choice are lyophilized and stored, they are used to isolate intact nucleic acid. The DNA and RNA isolated from the cells can be used for any suitable molecular biology application, including providing positive and negative controls for diagnostic and forensic assays. The nucleic acid can be used as a positive or negative control for a mutated gene or transcript. The nucleic acid can also serve as a positive or negative control for the presence of provirus, an episomal genome, a DNA or RNA genome, and transcripts from a viral genome. The nucleic acid can also be used to distinguish between different forms of a viral genome, for example between an integrated provirus and an episomal genome, either DNA or RNA. The nucleic acid can be used as a control for both genes and/or their transcripts and can distinguish between the two.

A number of reagents are useful for isolating intact RNA from the lyophilized cells. Each of these reagents lyses the cells and concomitantly minimizes or eliminates nuclease activity during the RNA isolation procedure: guanidine hydrochloride; guanidine isothiocyanate; sodium dodecyl sulfate or sarcosyl and proteinase K or pronase (see, e.g., Farrell, *RNA Methodologies* (1993)).

Standard laboratory techniques are used to isolate RNA from lyophilized cells (see, e.g., Sambrook et al., supra; Ausubel et al., supra). One preferred method of isolating RNA from cells is based on the method of Chomczynski, *Biotechniques* 15: 532–535 (1993)). This method uses a single reagent for isolation of RNA, or RNA and DNA. First, the cells are lysed using a guanidine isothiocyanate-phenol buffer. The sample is homogenized in this buffer and then separated into aqueous and organic phases by addition of chloroform and centrifugation. The RNA is then precipitated from the aqueous phase and resuspended in RNase free solution. DNA can also be isolated along with RNA using this technique. Kits based on this method are commercially available, e.g., the TRI Reagent® (Molecular Research Center, Inc.). A variety of other techniques can also be used to isolate RNA, such as those that use SDS/proteinase K treatment followed by extraction with a phenol solution. RNA can be further purified using centrifugation with a cesium chloride gradient. RNA can also be isolated using the silica gel binding/anion exchange method. DNA can be removed from the RNA by treating with RNase free DNase.

Standard laboratory techniques are used to isolate DNA from lyophilized cells. As described above, RNA and DNA can be isolated simultaneously, or DNA can be isolated, often by treating with RNase. Standard methods of isolating DNA from lyophilized cells usually include a step of lysing the cells, followed by deproteinization and recovery of the DNA (see, e.g., Ausubel et al., supra; Sambrook et al., supra). Commercial kits are also available for isolation of DNA from the lyophilized cells.

After nucleic acid is isolated from the lyophilized cells, it can be checked to make sure that it is intact. Typically, both RNA and DNA can be analyzed for integrity using gel electrophoresis according to standard procedures. After nucleic acid isolation, the concentration of the nucleic acid in solution is determined by standard spectrophotometric techniques, and then a standard amount is applied to a gel. After the electrophoresis is complete, the gel is stained with ethidium bromide, which allows visualization of the nucleic acid. For RNA, one indicator of intact RNA is the ratio of 28S rRNA to 18S rRNA. Based on a visual inspection of the gel, the rRNAs should be present as bands on the gel in a ratio of 28S rRNA to 18S rRNA of about at least 1. Preferably, the ratios of rRNA are higher than 1, e.g., 1.4–1.5. The ratio of 28S rRNA to 18S rRNA can also be measured, for example by densitometry of a picture of the gel. Another indication of intact RNA is background fluorescence throughout the gel due to the presence of mRNA. RNA stability can also be determined from the relative RNA yield as compared to freshly grown cells. Typically, cells lyophilized in isotonic solutions such as DEPC treated 1× PBS yield about the same amount of RNA as control cells that have been freshly grown and pelleted.

DNA integrity is also examined by gel electrophoresis. The intact genomic DNA should be present in relatively high molecular weights (generally ranging above about 10,000 bp in length, preferably above 20,000 bp in length). Episomal DNa can also be isolated in this manner. Both standard and pulsed field gel electrophoresis can be used to examine DNA.

VI. Diagnostic and forensic assays

Once the nucleic acid is isolated from the lyophilized cells, it can be used for a wide variety of applications. The present invention also provides lyophilized cells in vials for diagnostic and forensic applications, as well as kits for nucleic acid hybridization that include vials of lyophilized cells. Examples of the uses for the lyophilized cells of the invention include use in diagnostic assays such as cancers, genetic diseases, and infectious diseases, typically as assay controls.

The lyophilized cells and resulting intact nucleic acid isolated therefrom can be used in assays to detect infectious disease agents such as: human immunodeficiency virus ("HIV"), human papilloma virus ("HPV"), hepatitis viruses A, B, C, and D ("HAV, HBV, HCV, HDV"), cytomegalovirus ("CMV"), influenza virus, mycobacterium infection, trypanosome infection, and chlamydia infection (see, e.g., Castillo et al., *Digestion* 48: 149–156 (1991); Faulkner-Jones et al., *J. Virol. Methods* 41: 277–296 (1993); Meyer et al., *Mol. Cell. Probes* 8: 261–271 (1994); Mary et al., *J. Virol. Methods* 49: 9–23 (1994); and McPherson, *J. Clin. Lab. Anal.* 8: 369–377 (1994)). The cells and isolated nucleic acid can be used in assays to detect gene and mRNA changes associated with cancer such as p53, c-myc, pS2, BCR/ABL (see, e.g., Dante et al., *Lab. Invest.* 71: 188–192 (1994). The cells and nucleic acid can also be used in assays to detect genetic mutations associated with diseases, such as Ig rearrangements, β-thalassemia, cystic fibrosis, Huntington's chorea, and sickle cell anemia. The cells and nucleic acid are also useful in forensic and paternity assays involving, e.g., DNA fingerprinting (see, e.g., Budowle et al., *J. Forensic Sci.* 40: 38–44 (1995); Kasi et al., *J. Forensic Sci.* 35: 1196–1200 (1991).

Techniques used in diagnostic and forensic application include a wide variety of techniques based on nucleic acid hybridization e.g., northern blots, Southern blots, dot blots, DNA fingerprinting, RNase protection, and filter hybridization. One variation of nucleic acid hybridization techniques includes those based on nucleic acid amplification, such as reverse transcription ("RT"), polymerase chain reaction ("PCR"), ligase chain reaction ("LCR"), and nucleic acid sequence-based amplification ("NASBA").

Nucleic acid probes and primers used for hybridization assays are chosen to hybridize to a target gene or transcript. The probe can be a DNA or RNA molecule, as well as a synthetic, non-naturally occurring analog of the same. Hybridization conditions are selected by those skilled in the art, as discussed herein. Although primers and probes can differ in sequence and length, the primary differentiating factor is one of function: primers typically serve as an initiation point for DNA synthesis of a target nucleic acid, as in RT and PCR reactions, while probes are typically used for hybridization to and detection of a target nucleic acid. Typical lengths of primers or probes can range from about 7 to about 50 nucleotides. A primer or probe can also be labeled with a detectable moiety for detection of hybridization of the primer or probe to the target nucleic acid.

Any suitable method of detecting hybridization of a primer or probe to the target nucleic acid may be used. Detectable moieties used in these methods include, e.g., labelled probes; direct incorporation of label in amplification or RT reactions; and labelled primers.

One preferred hybridization assay is reverse transcription. Reverse transcription is an amplification method that copies RNA into DNA. The reverse transcription reaction, which synthesizes first strand cDNA, is typically performed by mixing RNA with random hexamer primer or a specific primer, heating to 70° C. for 5 minutes to denature the nucleic acids (a thermal cycler may be used for this step), and then cooling on ice. The reaction mixture, prepared according to the enzyme manufacturers instructions or according to kit instructions, is added to the denatured RNA and hexamer mixture and incubated at a suitable temperature, usually 42° C. The reaction is stopped by heating the tube containing the reaction mixture for 10 minutes at 70° C. The first strand cDNA is collected by precipitation and brief centrifugation and aliquoted to new tubes, in which it can be quickly frozen on dry ice and stored at −70° C., if necessary, for later use.

Another preferred type of hybridization assay are amplification based assays such as PCR (polymerase chain reaction) and LCR (ligase chain reaction). Standard techniques for performing such assays are known in the art (PCR Technology: *Principles and Applications for DNA Amplification* (Erlich, ed., 1989); *PCR Protocols: A Guide to Methods and Applications* (Innis, Gelfland, Sninsky, & White, eds., 1990); Mattila et al., *Nucleic Acids Res.* 19: 4967 (1991); Eckert & Kunkel, *PCR Methods and Applications* 1: 17 (1991); Wallace et al., *Ligase Chain Reaction, in Technologies for Detection of DNA Damage and Mutations,* pp. 307–322 (Pfiefer, ed., 1996)). RT and PCR reactions are often used in the same assay and are referred to as RT-PCR. RT-PCR combines reverse transcription of RNA into DNA and subsequent DNA amplification reactions in a single reaction. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., supra).

For example, PCR is typically carried out in a buffered aqueous solution, preferably at a pH of 7–9. Deoxyribonucleoside triphosphates are added to the synthesis mixture in adequate amounts, and the resulting solution may be heated to about 85–100° C. for about 1 to 10 minutes. After this optional heating period, the solution is allowed to cool to about 20–40° C., for primer hybridization. An agent for polymerization is added to the mixture, and the reaction is allowed to occur under conditions known in the art, typically using a thermocycler. This synthesis reaction may occur at room temperature up to a temperature just over which the agent for polymerization no longer functions efficiently. The agent for polymerization may be any compound or system that will function to accomplish the synthesis of primer extension products, including enzymes. Suitable enzymes for this purpose include, for example, E. coli DNA polymerase I or Klenow fragment, Taq DNA polymerase, and other available DNA polymerases.

The present invention also provides for kits for performing above-described the nucleic acid hybridization assays. Such kits can be prepared from readily available materials and reagents. For example, such kits can comprise any one or more of the following materials: lyophilized eukaryotic cells in vials, enzymes, reaction tubes, buffers, detergent, cell free primers and probes that target a known nucleic acid, and instructions. Preferably, the lyophilized cells of the kit are human cells. In one embodiment the human cells are lymphocytes. A wide variety of kits and components can be prepared according to the present invention, depending upon the intended user of the kit and the particular needs of the user. Preferably, the kit is for an amplification based assay such as PCR or LCR and includes at least one primer pair.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Formulations For Eukaryotic Cell Lyophilization

A. Real time/short term stability and RNA integrity of cells lyophilized in three different solutions Cell lyophilization formulations were tested to identify solutions that preserved the integrity of subsequently isolated nucleic acid. In this experiment, three formulations were used as cell resuspension solutions prior to lyophilization of eukaryotic cells ("lyophilization solutions"): (1) DEPC treated water; (2) 1× lactose buffer (12.5 mM TRIS, 35 mM NaCl, 1 mg/ml arginine, 5 mg/ml human serum albumin, and 50 mg/ml lactose, pH 7.4); and (3) TRI Reagent® (a commercially available phenol/guanidine isothiocyanate solution from Molecular Research Center, Inc.). Water was DEPC treated by adding 0.05%–0.1% DEPC to the water and then shaking the sealed container at room temperature for four hours. The solution was then autoclaved according to standard conditions and cooled. The short term stability of the lyophilized cells was examined by storing the cells at room temperature and at −70° C. for 5 days. RNA integrity after this storage period was measured by isolating total RNA from the lyophilized cells, along with RNA from freshly pelleted cells as a positive control. RNA integrity was determined by comparing the intensity of 28S to 18S RNA bands after gel electrophoresis.

The gel electrophoresis analysis demonstrated that total RNA isolated from SAM-1 cells lyophilized in DEPC treated water was approximately 50% degraded. The cells stored at room temperature and −70° C. for 5 days gave similar results for RNA integrity, indicted that short term stability of the cells under these conditions was similar. Total RNA from SAM-1 cells lyophilized in 1× lactose buffer or in TRI Reagent® was approximately 100% degraded.

These results indicate that although lactose and other isotonic carbohydrate formulations have been used successfully for lyophilization of bacterial cells, these solutions are not useful as lyophilization formulations for eukaryotic cells to preserve RNA integrity. Similarly, the TRI Reagent® is not useful for lyophilization of eukaryotic cells to preserve total RNA integrity.

SAM-1 cells were cultured using standard conditions in RPMI 1640 supplemented with 10% fetal bovine serum ("FBS") and antibiotics (see, e.g., Sambrook et al., supra). SAM-1 cells are a human tumor cell line that have the Philadelphia chromosome and the resulting fused BCR/ABL transcript. The culture was divided into three equal portions for resuspension in the three lyophilization formulations. The cells were pelleted under standard low speed centrifugation conditions and resuspended at a concentration of $1\times10^6$ cells per 100 µl in one of the solutions described above. 100–500 µl were aliquoted per vial for lyophilization.

The cells were lyophilized under standard conditions using an automated lyophilizer. The lyophilized cells were stored at both −70° C. and room temperature for 5 days before total RNA was isolated.

Total RNA from the lyophilized cell samples was isolated using the TRI Reagent® according to the manufacturer's instructions. The isolated total RNA was then analyzed using gel electrophoresis with a 1.5% agarose gel and 1× TAE buffer, according to standard procedures (see, e.g., Sambrook et al., supra; Ausubel et al., supra). The integrity of total RNA was estimated by staining the gel with ethidium bromide ("EtBr") and examining the intensity of bands for 28S, 18S, and 5.8S ribosomal RNA. Background EtBr staining present throughout the gel lane indicates the presence of mRNA in total RNA preparations. For intact RNA, the intensity of the 28S rRNA band should be equal to or higher than that of the 18S rRNA band, indicating the relative integrity of these larger sized RNA in total RNA preparations. As described above, this experiment, the RNA was approximately 50–100% degraded, as estimated by the relative intensity of the rRNA bands.

B. Stressed stability and RNA integrity of cells lyophilized in DEPC treated 1× PBS DEPC treated 1× PBS was tested to identify lyophilization solutions that preserved the integrity of subsequently isolated nucleic acid. The experiment described above in part A was repeated, substituting the following solutions as test formulations for cell lyophilization: (1) DEPC treated 1× phosphate buffered saline ("PBS"); and (2) DEPC treated water. 1× PBS is isotonic for human cultured cells. 1× PBS is commercially available in standard formulations and was DEPC treated as described above in part A.

Total RNA was isolated as described above in part A from lyophilized SAM-1 cells stored under stressed stability conditions at 37° C. for four days (equal to storage at −20° C. for more than 3 years), and from freshly grown cells as a control for RNA integrity. As measured by spectrophotometric analysis, gel electrophoresis and comparison of 18S and 28S rRNA, total RNA isolated from cells lyophilized in DEPC treated 1× PBS is intact after isolation with TRI Reagent®. Yields of total RNA obtained from lyophilized cells are nearly identical to those obtained from the control freshly grown cells. However, RNA isolated from cells lyophilized with DEPC treated water was partially degraded.

The stressed stability test results indicated that total RNA from cells lyophilized in either DEPC treated 1× PBS is stable at 37° C. for at least for 4 days (equivalent for storage at −20° C. for more than 3 years). In comparison, stressed stability tests performed as described in part C below indicate that the total RNA in cells lyophilized in DEPC treated water is mostly degraded.

In a second experiment performed as described above, cells lyophilized in DEPC treated 1× PBS were stored under different conditions. SAM-1 cells were lyophilized and stored under stressed stability conditions for two days at 25° C. Samples of HeLa S3 and SAM-1 cells were also lyophilized and stored for 3 months and 6 months, respectively at −20° C. RNA was isolated from each of the samples and RNA integrity was compared by densitometry of 28S and 18S rRNA.

FIG. 1 shows the stained gel picture used for a densitometry scan of 28S and 18S rRNA. The HeLa S3 (lanes N1–2) and SAM-1 (lanes P1–2) samples in this experiment were stored at −20° C., as described above. A second SAM-1 sample (lanes P3–4) was stored at 25° C. for 2 days. Table 1 shows the densitometry values obtained for the rRNA bands and the background from this gel, and the ratio of 28S to 18S rRNA after correction for background. These results demonstrate that total RNA is undegraded and stable when lyophilized in DEPC treated 1× PBS and stored under real time conditions at −20° C. or under stressed stability conditions equal to −20° C. for two years. The total RNA from all six of the samples also show the background mRNA staining and 5.8S rRNA band.

TABLE 1

28S/18S densitometry ratios

| Band | Sample | Densitometry value | Corrected 28S/18S ratio |
|---|---|---|---|
| V1 = 28S | HeLa S3 (N2) | 13.59 | 1.5 |
| V2 = 18S | HeLa S3 (N2) | 11.47 | |
| V3 = background | HeLa S3 (N2) | 7.29 | |
| V4 = 28S | SAM-1 (P2) | 13.33 | 1.4 |
| V5 = 18S | SAM-1 (P2) | 11.97 | |
| V6 = background | SAM-1 (P2) | 8.27 | |
| V7 = 28S | SAM-1 (P4) | 13.85 | 1.4 |
| V8 = 18S | SAM-1 (P4) | 12.19 | |
| V9 = background | SAM-1 (P4) | 8.05 | |

C. Stressed stability and RNA integrity of cells lyophilized in DEPC treated water This experiment was performed to investigate whether total RNA from different cells lyophilized in DEPC treated water can be isolated with high total RNA integrity. The stressed stability of total RNA in from cells lyophilized in DEPC treated water was examined.

SAM-1 and GM07405 cells were cultured and lyophilized as described above in part A, substituting DEPC treated water as the lyophilization formulation. GM07405 cells are a human lymphoblastic cell lines obtained from MIGMS Human Genetic Mutant Cell Repository, Coriell Institute for Medical Research, Camden, N.J. The lyophilized samples were stored at 37° C. for four days to measure stressed stability, as described above in part B. Total RNA was isolated from the lyophilized cells and compared to RNA isolated from freshly grown cells using gel electrophoresis analysis, as described above in part A.

Gel electrophoresis analysis indicated that total RNA isolated from SAM-1 cells lyophilized in DEPC treated water was partially degraded and total RNA isolated from GM07405 cells lyophilized in DEPC treated water was severely degraded. Microscopic observation demonstrated that this result was due to cell membrane disintegration for cells in DEPC treated water.

D. Stressed stability and RNA integrity of cells lyophilized in DEPC treated 1× PBS This experiment was performed to investigate whether total RNA from different cells lyophilized in DEPC treated 1× PBS can be isolated with high total RNA integrity. The lyophilized cells were stored under stressed stability conditions as described above in part B. Dr11 and SAM-1 cells were cultured and lyophilized as described above in part A, substituting DEPC treated 1× PBS as the lyophilization formulation. Dr11 cells are a human leukocytic cell line transformed with EBV. Total RNA was isolated as described above in part A using TRI Reagent® or the RNeasy kit (Qiagen), and RNA integrity was analyzed with gel electrophoresis.

The total RNA from the two different cell lines lyophilized in DEPC treated 1× PBS was intact as compared to the RNA from fresh cells. Furthermore, total RNA from the two different cell lines lyophilized in DEPC treated 1× PBS can be isolated with either TRI Reagent® or the RNeasy kit with high integrity and purity.

Stressed stability tests performed using the conditions described above in part B indicated that the total RNA in cells lyophilized in DEPC treated 1× PBS water is stable for more than 3 years when cells are stored at −20° C.

Example II

Use of SAM-1 and HeLa S3 Lyophilized Cells as Positive and Negative Controls For Diagnostic Assays This experiment was performed to demonstrate the effectiveness of using lyophilized cells as positive and negative controls in diagnostic assays. SAM-1 cells and HeLa S3 cells, respectively, were used as positive and negative controls in RT/PCR assays designed to detect transcripts of fused genes associated with chronic myelogenous leukemia ("CML").

A. The CML diagnostic assay

The Philadelphia chromosome is result of a translocation between chromosome 22 and chromosome 9 and is found in over 90% of CML cases (Rowley, Nature 243: 290–293 (1973); Shtivelman et al., Nature 315: 550–554 (1985)). At the molecular level, the c-ABL gene on chromosome 9 is translocated to the BCR gene on chromosome 22 in the Philadelphia chromosome, resulting in a BCR/ABL fused gene. This fusion gene also expresses fused RNA transcripts that can be detected using RT/PCR assays. For this assay, positive and negative control cells are required to provide standard for PCR amplicons and to monitor false positives and false negatives.

SAM-1 cells are useful as positive controls in this assay because they contain a BCR/ABL fusion gene that expresses fused transcripts, while HeLa S3 cells are useful negative controls because they contain only normal BCR and ABL genes expressing normal transcripts. Cells lyophilized in DEPC treated 1× PBS were tested in RT/PCR experiments to demonstrate the effectiveness of these lyophilized cells controls in this diagnostic assay.

The assay also includes a control for RNA integrity of the lyophilized cells. Both the cell lines constitutively express the β-2 microglobulin gene. Transcripts from this gene were therefore used as a control for the RNA integrity of the lyophilized cells in the RT/PCR reaction. Nearly 2000 vials of lyophilized SAM-1 cells and HeLa S3 cells were prepared for use as control cells in a commercial diagnostic kit designed for providing control materials for RT/PCR assays detection of the BCR/ABL fusion.

B. Lyophilization, RNA isolation and measurement of RNA integrity

Prior to use as controls in the CML diagnostic assays, the integrity of RNA isolated from lyophilized control cells was examined. RNA integrity was measured using three different techniques: total yield, optical density ratios, and gel electrophoresis analysis.

SAM-1 and HeLa S3 cells were lyophilized as described above in Example 1 and stored at −20° C. Total RNA was isolated from two vials each of the SAM-1 cells and HeLa S3 cells for RT/PCR of BCR/ABL transcripts and the B2M transcripts. The total RNA was prepared from lyophilized SAM-1 cells and HeLa S3 cells using the TRI Reagent® following a protocol modified from the one supplied by the manufacturer with a small modification for cell lysis. Lyophilized cells contained in vials were lysed directly by adding TRI Reagent® to vials without cell washing and cell pelleting before TRI Reagent® addition.

After total RNA preparation, the final RNA pellet was rehydrated in DEPC treated and amplicon-free water. A fraction of the rehydrated total RNA can be used for optical density determinations at 260 nm and 280 nm for concentration determination. The μg yields of the total RNA preparations were estimated using 1 OD at A260 equals 40 μg of total RNA in water. For cells lyophilized in DEPC treated 1× PBS, the yield was essentially the same for the lyophilized cells as that from freshly grown cells used as a control. The μg yields of the total RNA solutions are listed in Table 2 below.

TABLE 2

Yield of total RNA obtained from lyophilized SAM-1 and HeLa S3 cells

| Vial # | Lyophilized cells | Total RNA yields |
| --- | --- | --- |
| 1 | HeLa S3 | 25.2 μg |
| 2 | HeLa S3 | 26.6 μg |
| 1 | SAM-1 | 40.6 μg |
| 2 | SAM-1 | 43.3 μg |

Integrity of RNA can also be estimated by measuring optical absorption of RNA solutions at 260 nm and 280 n. Pure RNA preparations should have A260/A280 ratios between 1.6 to 1.9. As shown in Table 3 below, total RNA prepared from duplicate vials of lyophilized SAM-1 cells and HeLa s3 cells all have A260/A280 ratios between 1.6 and 1.8, demonstrating the high purity of total RNA.

TABLE 3

A260/A280 ratios of total RNA

| Vial | Lyophilized cells | A260/A280 |
| --- | --- | --- |
| 1 | HeLa S3 | 1.63 |
| 2 | HeLa S3 | 1.68 |
| 1 | SAM-1 | 1.79 |
| 2 | SAM-1 | 1.75 |

A third method for assessing integrity of total RNA involves agarose gel analysis of total RNA solutions using 1.5% agarose gel and 1× TAE buffer. Following electrophoresis, the integrity of total RNA is estimated by staining with ethidium bromide ("EtBr") and examining the intensity of bands for 28S, 18S and 5.8S ribosomal RNAs, as described above in Example 1. EtBr stained lanes containing the total RNA isolated from 2 vials each of the lyophilized SAM-1 cells and HeLa S3 cells displayed typical patterns of total RNA from human cells. Moreover, the relative ratios of the 28S and the 18S bands also indicated the high integrity of total RNA (see Table 1). These results indicate that the integrity of total RNA isolated from lyophilized SAM-1 and HeLa S3 cells using the TRI Reagent® is appropriate for use as a diagnostic assay control.

C. RT reactions

Figure 2:
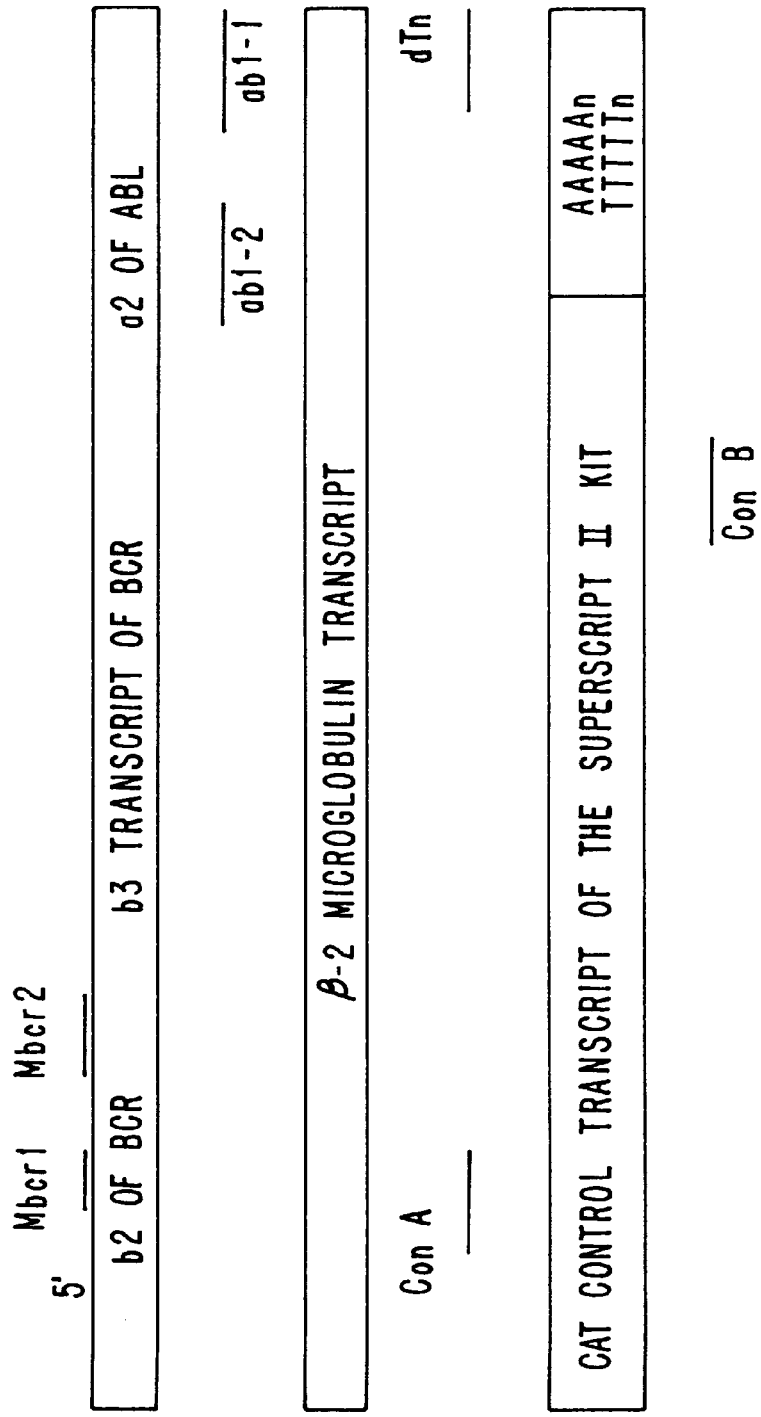
FIG. 2 shows a diagram of PCR primers used for amplification of the BCR/ABL fused mRNA, β-2 microglobulin mRNA, and CAT mRNA.

After RNA is isolated from lyophilized cells, it was reverse transcribed and used as positive and negative controls for diagnostic CML assays (see, e.g., Kawasaki et al., PNAS USA 85: 5698–5702 (1988)). This RT/PCR assay for detecting MRNA resulting from BCR/ABL fused genes typically included the steps of (1) cDNA preparation from total RNA using reverse transcriptase; (2) nested PCR with BCR and ABL primers; (3) a two-round PCR of β-2 microglobulin (B2M); and (4) agarose gel analysis of PCR amplicons. See FIG. 2 and Tables 4–5 for a description of the primers used in this assay.

Standard reaction conditions and a commercially available kit were used to reverse transcribe cDNA from 1 μg of total RNA from lyophilized SAM-1 and HeLa S3 cells. The CAT transcript is provided as a control for RT/PCR efficiency in the commercial kit. The commercial cDNA preparation kit used was the 'SuperScript™ Preamplification System for First Strand cDNA Synthesis kit (GibcoBRL/ Life Technologies). In addition to a primer and Superscript II RT enzyme, each cDNA reaction also contained 10× PCR buffer, MgCl$_2$, dNTP mix, DTT, and RNase H. The protocol used is identical to that supplied by the manufacturer of the kit. Specific RT primers described below in Table 4 were used for the RT reaction. Primers for the CAT RNA are described in the 'Super Script™ instruction manual (GibcoBRL/Life Technologies). Primers for the BCR/ABL and the β-2 microglobulin transcripts are described in Lee et al., PCR Methods and Applications 4: 283–287 (1995). See FIG. 2 for the diagram of the primers and their relative positions on the gene/transcript.

D. Description of RT/PCR primers

TABLE 4

Names of oligonucleotide primers used for RT/PCR

| Specific Gene | cDNA primers | PCR #1 primers | PCR #2 primers |
| --- | --- | --- | --- |
| CAT gene | (dT)n | Con A Con B | Con B Con B |
| β2 microglobulin | 3' B2M | 5' B2M | 5' B2M; |

TABLE 4-continued

Names of oligonucleotide primers used for RT/PCR

| Specific Gene | cDNA primers | PCR #1 primers | PCR #2 primers |
|---|---|---|---|
| gene BCR/ABL gene | abl-2 | 3' B2M Mbcr-1 abl-1 | 3' B2M Mbcr-2; abl-2 |

TABLE 5

Sequences of oligonucleotide primers used for RT/PCR

| Oligo name | Gene | Primer Use | Sequence (5' to 3') |
|---|---|---|---|
| (dT)n | CAT | cDNA | (dT)n (n = 12 to 18) (SEQ ID NO: 9) |
| Con A | CAT | PCR #1 PCR #2 | GAC ATG GAA GCC ATC ACA GAC (SEQ ID NO:1) |
| Con B | CAT | PCR#1 PCR #2 | CGA CCG TTC AGC TGG ATA TTA C (SEQ ID NO:2) |
| Mbcr-1 | BCR | PCR #1 | GAA GTG TTT CAG AAG CTT CTC C (SEQ ID NO:3) |
| Mbcr-2 | BCR | PCR #2 | TGG AGC TGC AGA TGC T (SEQ ID NO:4) |
| abl-1 | ABL | cDNA PCR #1 | TGA TTA TAG CCT AAG ACC CGG A (SEQ ID NO:5) |
| abl-2 | ABL | PCR #2 | ATC TCC ACT GGC CAC AA (SEQ ID NO:6) |
| 3' B2M | B2M | PCR#1 PCR #2 | CCT CCA TGA TGC TGC TTA CAT GTC (SEQ ID NO:7) |
| 5' B2M | B2M | cDNA PCR #1 PCR #2 | ATG TCT CGC TCC GTG GCC TTA GCT (SEQ ID NO:8) |

TABLE 6

Expected final amplicon sizes of the CAT, B2M, and BCR/ABL fused genes

| Template | PCR of CAT control gene | PCR of the BCR/ABL gene | PCR of the B2M gene |
|---|---|---|---|
| total RNA of lyophilized SAM-1 cells | (NA) | 304 bp amplicon | 370 bp amplicon |
| total RNA of lyophilized HeLa S3 | (NA) | no amplicon | 370 bp amplicon |
| CAT gene control RNA | 530 bp amplicon | (NA) | (NA) |

E. PCR reaction conditions

The assay for detecting BCR/ABL fused transcripts typically included the following reactions: (1) nested PCR with BCR and ABL primers; (2) a control PCR reaction for β2-microglobulin transcripts (B2M) (to measure RNA integrity); and (3) a control PCR reaction for CAT (to measure RT/PCR efficiency). The RT/PCR samples were analyzed with agarose gel analysis of PCR amplicons. The BCR/ABL RT/PCR assay used nested PCR with an inner set primer for one reaction and an outer primer set for one reaction, respectively (see FIG. 2). The PCR of the B2M gene also includes two consecutive PCR reactions using the same primer pair in first round PCR and the second round PCR (see FIG. 2).

In the first PCR reaction, 5 μl of cDNA (of 20 μl total volume of cDNA) prepared from total RNA of SAM-1 cells and HeLa S3 cells was used as the template source. In the second PCR reaction, 1 μl of the first PCR was used as the template source.

The following cycling conditions were used in the PCR reactions of the diagnostic assay:

PCR #1:

| 1 cycle | 94° C., 5 min. + |
| 25 cycles | 94° C., 1 min., 60° C., 25 sec.; 74° C., 1 min. |
| 1 cycle | 74° C., 8 min. |

PCR #2:

| 1 cycle | 94° C., 3 min. + |
| 25 cycles | 94° C., 1 min., 48° C., 25 sec.; 74° C., 1 min. |
| 1 cycle | 74° C., 8 min. |

The PCR reaction contained 10× PCR buffer (with MgCl$_2$, from Perkin Elmer; AmpliTaq DNA polymerase; dATP, dTTP, dGTP, dCTP stocks (10 mM each); amplicon-free water; cDNA templates; and PCR primers, 10 μM in TE buffer. The final concentrations of these components in the reactions are described below in Tables 7 and 8, with a final reaction volume of 50 μl. cDNA templates used in different RT/PCR reactions are listed in Table 9 below. For PCR #2, 1 μl of the PCR #1 reaction was added to PCR #2 as the template source.

TABLE 7

PCR #1 reaction components

| | Stock conc'n | Final conc'n |
|---|---|---|
| Amplicon-free water | | add to final 50 μl per PCR |
| PCR buffer | 10 X | 1 X |
| dNTP's | a mixture of 2.5 mM each of 4 dNTP's | 0.2 mM each of 4 dNTP's |
| Con A, Con B primer | 1 X (as supplied in kit) | 0.01 X per PCR |
| Mbcr-1, abl-1 | 10 μM | 0.2 μM each |
| 3' B2M, 5' B2M | 10 μM | 0.2 μM each |
| cDNA templates | | 5 μl out of 20 μl cDNA reaction mixtures |
| AmpliTaq DNA polymerase | 5 U/μl | 0.05 U/μl |

TABLE 8

PCR #2 reaction components

| | Stock conc'n | Final conc'n |
|---|---|---|
| Amplicon-free water | — | add to final 50 μl per PCR |
| PCR buffer | 10 X | 1 X |
| dNTP's | a mixture of 2.5 mM each of 4 dNTP's | 0.2 mM each of 4 dNTP's |
| Con A, Con B primer | 1 X (as supplied in kit) | 0.01 X per PCR |
| Mbcr-1, abl-1 | 10 μM | 0.4 μM each |
| 3' B2M, 5' B2M | 10 μM | 0.4 μM each |
| AmpliTaq DNA polymerase | 5 U/μl | 0.05 U/μl |

TABLE 9 cDNA templates in PCR reactions

| | | | | | | | | | |
|---|---|---|---|---|---|---|---|---|---|
| Reaction tube numbers of PCR of BCR/ABL RT/PCR | 1 CAT control | 2 | 3 | 4 | 5 | 6 | 7 | 8 | 9 |
| Reaction tube numbers of PCR #1, #2 of B2M RT/PCR | 11 CAT control | 12 | 13 | 14 | 15 | 16 | 17 | 18 | 19 |
| total RNA source for cDNA preps | CAT RNA cont. | SAM | SAM | HeLa | HeLa | SAM no RT | HeLa no RT | SAM no Taq | HeLa no Taq |
| RT enz. | + | + | + | + | + | none | none | + | + |
| Taq | + | + | + | + | + | + | + | none | none |

F. RT/PCR results

The overall results of this experiment demonstrate the effectiveness of using lyophilized SAM-1 cells and HeLa S3 cells as positive control cells, and negative control cells, respectively, in RT/PCR for detecting BCR/ABL fused genes. Control cells can be used from the first step (the total RNA isolation step) of RT/PCR along with test sample cells. The protocol for RNA isolation from lyophilized cells is relatively easy, using commonly used total RNA reagents. Moreover, the final ethidium bromide stained agarose gel provides clear amplicon size standards to be used for RT/PCR of the BCR/ABL fused genes and the β2 microglobulin gene. All negative control PCR reactions performed without AmpliTaq or without RT did not produce any amplicon bands.

For example, specific 523 bp amplicons were produced from PCR reactions using a cDNA template from CAT control RNA supplied in the SuperScript II kit. This result indicates the high efficiencies of the cDNA reaction and PCR reactions.

Approximately equal amounts of specific 370 bp amplicons were produced from PCR reactions of the β2 microglobulin (B2M) transcript with cDNA template from lyophilized SAM-1 cells and lyophilized HeLa S3 cells. This result indicates the presence of nearly equal amounts of the normal B2M RNA in lyophilized SAM-1 cells and HeLa S3 cells.

Specific 304 bp amplicons were produced from nested PCR of the BCR/ABL gene with cDNA templates prepared from lyophilized SAM-1 cells, but not from lyophilized HeLa S3 cells. This result indicates the presence of the BCR/ABL MRNA only in the lyophilized SAM-1 cells, not in HeLa S3 cells.

Example III

Use of SAM-1 and Dr11 Lyophilized Cells as Positive and Negative Controls For Diagnostic Assays The experiment described above in Example II was repeated, substituting Dr11 cells for HeLa S3 cells. This experiment yielded similar results.

Example IV

Use of DNA From Lyophilized Cells as a Diagnostic Control

Genomic DNA was isolated from lyophilized SAM-1 cells and Dr11 cells to demonstrate the integrity of DNA in lyophilized cells and the use of lyophilized cells as controls for DNA assays.

Genomic DNA was isolated from lyophilized cultured SAM-1 cells and Dr11 cells using commercial DNA isolation kits or a common cell lysis method using high concentration of sodium lauryl sulfate. Integrity of the DNA was analyzed using agarose gel electrophoresis under standard conditions (see, e.g. Sambrook et al., supra; Ausubel et al., supra). After staining with ethidium bromide under standard conditions, the DNA was primarily represented at high molecular weights, indicating that it was relatively undegraded.

These results from agarose gel analysis indicate similar yields and integrity of DNA can be obtained from lyophilized and freshly grown Dr11 and SAM-1 cells. In addition, similar to stability of RNA, genomic DNA isolated from lyophilized Dr11 cells and SAM-1 cells was also found to be stable for more than 1 year when stored at −20° C. for DNA isolation. Results obtained from pulse-field gel analysis performed on genomic DNA demonstrated the size and yields of DNA isolated from either freshly grown cells or lyophilized cells are highly similar for both cell lines tested.

To further demonstrate the integrity of DNA isolated from lyophilized cells, genomic DNA isolated from either Dr11 cells or SAM-1 cells were used in PCR of the ABL gene and the z-finger gene. The sizes of the amplicons obtained for the z-finger gene and the ABL gene in RT/PCR experiment were approximately 350 bp and 1000 bp, respectively (these sizes were as expected from the known sequence of both genes). Nearly identical yields of amplicons can be obtained from 100 ng of genomic DNA isolated from lyophilized or freshly grown Dr11 cells or SAM-1 cells for both the ABL gene or the z-finger gene.

In a similar experiment, PCR was performed using DNA isolated from the Dr11 and SAM-1 cells as templates and two oligonucleotides selected from a VNTR marker (DIS80) as PCR primers (Kasai et al., supra). The DIS80 locus, located on human chromosome 1, is composed of repeating units of 16 nucleotide long DNA. The number of repeats is reported to range from 15 to 41 in different individuals (Budowle et al., supra). This variability in the number of repeats in the DIS80 gene is the basis for DNA fingerprinting (DNA profile) analysis.

PCR performed on the DIS80 marker using DNA isolated from the Dr11 and SAM-1 cells yielded distinct amplicon pairs with different sizes. Sizes of amplicons obtained from PCR using DNA templates from either lyophilized cells or freshly grown cells are identical indicating the DIS80 DNA was preserved in the lyophilized cells. These results indicate that the lyophilized cells are a good source of control cells for DNA finger-printing and gene profiling experiments. The lyophilized cells provide a stable source of DNA that can be used as controls for different types of tests.

---

What is claimed is:

1. A method for long term preservation of nucleic acid contained within eukaryotic cells the method comprising:

i. contacting intact eukaryotic cells with an isotonic, nuclease-free aqueous solution, wherein the aqueous solution has been treated with diethyl pyrocarbonate;

ii. lyophilizing the intact eukaryotic cells; and, iii. maintaining the lyophilized cells under sealed conditions sufficient to avoid contact with atmospheric humidity, wherein the cells after 4 weeks at −20° C. have more than 50% of their 18S rRNA intact as measured by gel electrophoresis.

2. A method of claim 1 wherein the aqueous solution comprises sodium chloride at a concentration of between 0.8 and 1.0% by weight to volume.

3. A method of claim 1 wherein the eukaryotic cells are mammalian.

4. A method of claim 3 wherein the cells are human.

5. A method of claim 1 wherein the aqueous solution comprises a phosphate buffered saline solution.

6. A method of claim 1 wherein the pH of the solution is between 6.8 and 8.2.

7. A method of claim 1 wherein the cells are lymphocytes.

8. A method of claim 1 wherein the cells are cultured prior to lyophilization.

9. A method of claim 1 wherein the cells are infected with an RNA virus.

10. A method of claim 4 wherein the cells have a chromosomal translocation that results in a BCR/ABL fused gene.

11. A method of claim 4 wherein the cells are SAM-1 cells.

* * * * *